(12) United States Patent
Reyes et al.

(10) Patent No.: US 8,119,576 B2
(45) Date of Patent: Feb. 21, 2012

(54) CERAMIC COATED PARTICULATES

(75) Inventors: Enrique A. Reyes, Duncan, OK (US);
Jimmie D. Weaver, Duncan, OK (US);
Hongyu Luo, Duncan, OK (US)

(73) Assignee: Halliburton Energy Services, Inc.,
Duncan, OK (US)

( * ) Notice: Subject to any disclaimer, the term of this patent is extended or adjusted under 35 U.S.C. 154(b) by 164 days.

(21) Appl. No.: 12/574,018

(22) Filed: Oct. 6, 2009

(65) Prior Publication Data

US 2010/0093566 A1    Apr. 15, 2010

Related U.S. Application Data

(60) Provisional application No. 61/104,610, filed on Oct. 10, 2008, provisional application No. 61/104,620, filed on Oct. 10, 2008, provisional application No. 61/104,624, filed on Oct. 10, 2008, provisional application No. 61/104,629, filed on Oct. 10, 2008.

(51) Int. Cl.
| | |
|---|---|
| *C23F 11/18* | (2006.01) |
| *C09K 8/74* | (2006.01) |
| *C09K 8/68* | (2006.01) |
| *E21B 43/04* | (2006.01) |
| *A47B 43/00* | (2006.01) |
| *E21B 43/267* | (2006.01) |
| *E21B 43/26* | (2006.01) |

(52) U.S. Cl. ........ 507/271; 507/269; 507/273; 166/278; 166/279; 166/280.1; 166/280.2; 166/305.1

(58) Field of Classification Search .................. 507/269, 507/271, 273; 166/278, 279, 280.1, 280.2, 166/305.1
See application file for complete search history.

(56) References Cited

U.S. PATENT DOCUMENTS

| | | |
|---|---|---|
| 3,163,212 A | 12/1964 | Bermard |
| 3,323,595 A | 6/1967 | Knox et al. |
| 3,343,599 A | 9/1967 | Eddins, Jr. et al. |
| 3,437,145 A | 4/1969 | Johnson et al. |
| 3,438,443 A | 4/1969 | Prats et al. |
| 3,443,637 A | 5/1969 | Bond et al. |
| 3,815,680 A | 6/1974 | McGuire et al. |
| 4,074,536 A | 2/1978 | Young |
| 4,232,740 A | 11/1980 | Park |
| 4,323,124 A | 4/1982 | Swan |
| 4,425,384 A | 1/1984 | Brownscombe |
| 4,432,881 A | 2/1984 | Evani |
| 4,460,627 A | 7/1984 | Weaver et al. |
| 4,475,595 A | 10/1984 | Watkins et al. |
| 4,487,867 A | 12/1984 | Almond et al. |
| 4,572,296 A | 2/1986 | Watkins |
| 4,579,176 A | 4/1986 | Davies et al. |
| 4,582,137 A | 4/1986 | Schmitt |
| 4,585,064 A | 4/1986 | Graham et al. |
| 4,606,227 A | 8/1986 | Walters |
| 4,681,854 A | 7/1987 | Feazel |
| 4,814,096 A | 3/1989 | Evani |
| 4,838,351 A | 6/1989 | Jennings, Jr. et al. |
| 4,892,147 A | 1/1990 | Jennings, Jr. et al. |
| 4,898,750 A | 2/1990 | Friedman et al. |
| 4,913,236 A | 4/1990 | Reed |
| 4,922,758 A | 5/1990 | Penny |
| 4,997,582 A | 3/1991 | Clark, Jr. et al. |
| 5,042,581 A | 8/1991 | Jennings, Jr. et al. |
| 5,211,235 A | 5/1993 | Shu et al. |
| 5,240,075 A | 8/1993 | Burrows et al. |
| 5,249,627 A | 10/1993 | Harms et al. |
| 5,277,823 A | 1/1994 | Hann et al. |
| 5,393,439 A | 2/1995 | Laramay et al. |
| 5,529,125 A | 6/1996 | Di Lullo Arias et al. |
| 5,558,171 A | 9/1996 | McGlothlin et al. |
| 5,582,249 A | 12/1996 | Caveny et al. |
| 5,604,184 A | 2/1997 | Ellis et al. |
| 5,721,313 A | 2/1998 | Young et al. |
| 5,775,425 A | 7/1998 | Weaver et al. |
| 5,787,986 A | 8/1998 | Weaver et al. |
| 5,833,000 A | 11/1998 | Weaver et al. |
| 5,839,510 A | 11/1998 | Weaver et al. |
| 5,853,048 A | 12/1998 | Weaver et al. |
| 5,867,549 A | 2/1999 | Lindquist et al. |
| 6,069,108 A | 5/2000 | Ernst et al. |
| 6,070,664 A | 6/2000 | Dalrymple et al. |
| 6,153,106 A | 11/2000 | Kelley et al. |
| 6,311,773 B1 | 11/2001 | Todd et al. |

(Continued)

FOREIGN PATENT DOCUMENTS

EP    0082657 A2    6/1983

(Continued)

OTHER PUBLICATIONS

Okoye et al, "Characterization of Formation Damage in Heavy Oil Formation During Steam Injection," SPE 19417, 1990.
Shuchart et al., "Improved Success in Acid Stimulations with a New Organic-HF System," SPE 36907, 1996.
Gdanski et al., "Advanced Sandstone Acidizing Designs Using Improved Radial Models," SPE 38597, 1997.
Stanely et al., "Matrix Acidizing Horizontal Gravel-Packed Wells for Fines Damage Removal," SPE 65519, 2000.
Wennberg et al., "Successful Mud Acid Stimulations Maintain Productivity in Gravelpacked Wells at Heidrun," SPE 68925, 2001.
Husen et al., "Chelating Agent-Based Fluids for Optimal Stimulation of High-Temperature Wells," SPE 77366, 2002.
Ali et al., "Stimulation of High-Temperature Sandstone Formations from West Africa with Chelating Agent-Based Fluids," SPE 93805, 2008.

(Continued)

*Primary Examiner* — Timothy J. Kugel
*Assistant Examiner* — Atnaf Admasu
(74) *Attorney, Agent, or Firm* — Robert A. Kent; McDermott Will & Emery LLP

(57) ABSTRACT

Treatments and compounds useful in subterranean formations are discussed, with particular attention to those utilizing ceramic coated particulates. Certain embodiments pertain to particulates and particulate packs with ceramic coatings of subatomic thickness. Of these, certain methods may utilize ceramic coatings on particulates in a subterranean formation, certain methods may utilize ceramic coatings on particulate packs in a subatomic formation, and certain compounds may provide the features of both ceramic coatings and particulates.

11 Claims, No Drawings

U.S. PATENT DOCUMENTS

| | | |
|---|---|---|
| 6,439,309 B1 | 8/2002 | Matherly et al. |
| 6,461,518 B1 | 10/2002 | Demadis et al. |
| 6,476,169 B1 | 11/2002 | Eoff et al. |
| 6,531,427 B1 | 3/2003 | Shuchart et al. |
| 6,547,871 B2 | 4/2003 | Chatterji et al. |
| 6,660,693 B2 | 12/2003 | Miller et al. |
| 6,729,408 B2 | 5/2004 | Hinkel et al. |
| 6,877,563 B2 | 4/2005 | Todd et al. |
| 6,920,928 B1 | 7/2005 | Davies et al. |
| 7,021,383 B2 | 4/2006 | Todd et al. |
| 7,040,403 B2 | 5/2006 | Nguyen et al. |
| 7,091,159 B2 | 8/2006 | Eoff et al. |
| 7,114,568 B2 | 10/2006 | Eoff et al. |
| 7,131,491 B2 | 11/2006 | Blauch et al. |
| 7,159,656 B2 | 1/2007 | Eoff et al. |
| 7,159,659 B2 | 1/2007 | Welton et al. |
| 7,192,908 B2 | 3/2007 | Frenier et al. |
| 7,201,844 B1 | 4/2007 | Hammen et al. |
| 7,207,387 B2 | 4/2007 | Eoff et al. |
| 7,216,705 B2 | 5/2007 | Saini et al. |
| 7,216,707 B2 | 5/2007 | Eoff et al. |
| 7,220,708 B2 | 5/2007 | Zamora et al. |
| 7,273,099 B2 | 9/2007 | East, Jr. et al. |
| 7,316,787 B2 | 1/2008 | Hendel et al. |
| 7,347,264 B2 | 3/2008 | Nguyen |
| 7,363,978 B2 | 4/2008 | Welton et al. |
| 7,398,825 B2 | 7/2008 | Nguyen et al. |
| 7,500,519 B2 | 3/2009 | Weaver et al. |
| 7,552,771 B2 | 6/2009 | Eoff et al. |
| 7,563,750 B2 | 7/2009 | Eoff et al. |
| 7,589,048 B2 | 9/2009 | Eoff et al. |
| 7,591,313 B2 | 9/2009 | Weaver et al. |
| 7,595,283 B2 | 9/2009 | Eoff et al. |
| 7,741,251 B2 | 6/2010 | Eoff et al. |
| 7,759,292 B2 | 7/2010 | Eoff et al. |
| 2003/0188872 A1 | 10/2003 | Nguyen et al. |
| 2004/0209780 A1 | 10/2004 | Harris et al. |
| 2004/0229756 A1 | 11/2004 | Eoff et al. |
| 2005/0049151 A1 | 3/2005 | Nguyen et al. |
| 2005/0070679 A1 | 3/2005 | Breuer et al. |
| 2005/0079981 A1 | 4/2005 | Nguyen et al. |
| 2005/0092489 A1 | 5/2005 | Welton et al. |
| 2005/0107263 A1 | 5/2005 | Bland et al. |
| 2005/0148721 A1 | 7/2005 | Tonapi et al. |
| 2005/0150838 A1 | 7/2005 | Duke et al. |
| 2005/0155796 A1 | 7/2005 | Eoff et al. |
| 2005/0194140 A1 | 9/2005 | Dalrymple et al. |
| 2005/0199396 A1 | 9/2005 | Sierra et al. |
| 2005/0277554 A1 | 12/2005 | Blauch et al. |
| 2006/0035790 A1 | 2/2006 | Okell et al. |
| 2006/0118300 A1 | 6/2006 | Welton et al. |
| 2006/0137875 A1 | 6/2006 | Duserhoft et al. |
| 2006/0180309 A1 | 8/2006 | Welton et al. |
| 2006/0180310 A1 | 8/2006 | Welton et al. |
| 2006/0183646 A1 | 8/2006 | Welton et al. |
| 2006/0260808 A1 | 11/2006 | Weaver et al. |
| 2006/0264332 A1 | 11/2006 | Welton et al. |
| 2006/0266522 A1 | 11/2006 | Eoff et al. |
| 2006/0283592 A1 | 12/2006 | Sierra et al. |
| 2007/0015669 A1 | 1/2007 | Zhang |
| 2007/0079965 A1 | 4/2007 | Nguyen et al. |
| 2007/0235189 A1 | 10/2007 | Milne et al. |
| 2007/0281110 A1 | 12/2007 | Brown |
| 2007/0289781 A1 | 12/2007 | Rickman et al. |
| 2008/0011687 A1 | 1/2008 | Campo et al. |
| 2008/0035339 A1 | 2/2008 | Welton et al. |
| 2008/0035340 A1 | 2/2008 | Welton et al. |
| 2008/0110812 A1 | 5/2008 | Jensen et al. |
| 2008/0132711 A1 | 6/2008 | Poelker et al. |
| 2008/0135245 A1* | 6/2008 | Smith et al. ............... 166/280.2 |
| 2008/0280789 A1 | 11/2008 | Welton et al. |
| 2009/0111718 A1 | 4/2009 | Gadiyar et al. |
| 2009/0143258 A1 | 6/2009 | Welton et al. |
| 2009/0221454 A1 | 9/2009 | Welton et al. |
| 2009/0233819 A1 | 9/2009 | Fuller et al. |
| 2009/0271501 A1 | 10/2009 | Shenfield et al. |
| 2009/0291863 A1 | 11/2009 | Welton et al. |
| 2009/0312201 A1 | 12/2009 | Huang et al. |
| 2010/0021552 A1 | 1/2010 | Hayes et al. |
| 2010/0089578 A1 | 4/2010 | Nguyen et al. |
| 2010/0089579 A1 | 4/2010 | Reyes et al. |
| 2011/0079392 A1 | 4/2011 | Reyes |
| 2011/0253374 A1 | 10/2011 | Reyes et al. |

FOREIGN PATENT DOCUMENTS

| | | |
|---|---|---|
| FR | 2858314 | 2/2005 |
| GB | 2298440 A | 9/1996 |
| WO | WO0051945 | 9/2000 |
| WO | WO 03/015523 A2 | 2/2003 |
| WO | WO 03/097996 A1 | 11/2003 |
| WO | WO 2004/096940 A1 | 11/2004 |
| WO | WO 2004/104135 A1 | 12/2004 |
| WO | WO2005/100007 A2 | 10/2005 |
| WO | WO 2006/123143 A1 | 11/2006 |
| WO | WO2007/013883 A2 | 2/2007 |
| WO | WO2007051167 A3 | 5/2007 |
| WO | WO 2007/091058 A1 | 8/2007 |
| WO | WO 2008/015464 A1 | 2/2008 |
| WO | WO 2008/094069 A2 | 8/2008 |
| WO | WO2009085377 A1 | 7/2009 |

OTHER PUBLICATIONS

Ali et al., "Effective Stimulation of High-Temperature Sandstone Formations in East Venezuela with a New Sandstone-Acidizing System," SPE 98318, 2006.

Xiao et al., "Reactive Transport Modeling of Carbonate and Siliciclastic Diagenesis and Reservoir Quality Prediction," SPE 101669, 2006.

Aboud et al., "Effective Matrix Acidizing in High-Temperature Environments," SPE 109818, 2007.

Falcone et al., "Oil and Gas Expertise for Geothermal Exploitation: The Need for Technology Transfer," SPE 113852, 2008.

Kerkar et al., "Assessment of Dynamic Filtration Formation Damage for Alaskan North Slope Drilling Fluids," SPE 114142, 2008.

Huang et al., "Using Nanoparticle Technology to Control Formation Fines Migration," SPE 115384, 2008.

Pedenaud et al., "A New Water Treatment Scheme for Thermal Development: The SIBE Process," SPE/PS/CHOA 117561, PS 2008-304, 2008.

Gomez et al., "Acid Stimulation of Geothermal Wells in Central America," SPE 121300, 2008.

Weaver et al., "A Study of Proppant-Formation Reactions," SPE 121465, 2009.

Neofotistou et al., "Silica Scale Inhibition by Polyaminoamide STARBURST® Dendrimers," Colloids and Surfaces A: Physicochem. Eng. Aspects 242 (2004) 213-216.

Mavredaki et al., "Inhibition and Dissolution as Dual Mitigation Approaches for Colloidal Silica Fouling and Deposition in Process Water Systems: Functional Synergies," Ind. Eng. Chem. Res. (2005), 44, 7019-7026.

Demadis et al., "Solubility Enhancement of Silicate with Polyamine/Polyammonium Cationic Macromolecules: Relevance to Silica-Laden Process Waters," Ind. Eng. Chem. Res. (2006), 45, 4436-4440.

Demadis et al., "Industrial Water Systems: Problems, Challenges and Solutions for the Process Industries," Desalination(2007), 213, 38-46.

Demadis,et al., "Inhibitory Effects of Multicomponent, Phosphonate-Grafted, Zwitterionic Chitosan Biomacromolecules on Silicic Acid Condensation," Biomacromolecules (2008), 9, 3288-3293.

Stathoulopoulou et al., "Enhancement of Silicate Solubility by Use of 'Green' Additives: Linking Green Chemistry and Chemical Water Treatment," Desalination (2008), 224, 223-230.

Ketsetzi et al., "Being 'Green' in Chemical Water Treatment Technologies: Issues, Challenges and Developments," Desalination (2008), 223, 487-493.

Euvrard et al., "Influence of PPCA (Phosphinopolycarboxylic Acid) and DETPMP (Diethylenetriaminepentamethylenephosphonic Acid) on Silica Fouling," Desalination 205 (2007) 114-123.

Esumi et al., "Adsorption of Poly(Amidoamine) Dendrimers on Alumina/Water and Silica/Water Interfaces," Langmuir (1998), 14, 4466-4470.

Laird et al., "Elemental Recoveries for Clay Minerals Analysed by Inductively Coupled Plasma Atomic Emission Spectrometry Using Slurry Nebulisation," Journal of Analytical Atomic Spectrometry, vol. 5, (Sep. 1990).

Hamrouni et al., "Analytical Aspects of Silica in Saline Waters—Application to Desalination of Brackish Waters," Desalination 136 (2001) 225-232.

Strekopytov et al., "The Formation, Precipitation and Structural Characterisation of Hydroxyaluminosilicates Formed in the Presence of Fluoride and Phosphate," Polyhedron 24 (2005) 1585-1592.

Azaroual et al., "Solubility of Silica Polymorphs in Eletrolyte Solutions, I. Activity Coefficient of Aqueous Silica from 25° to 250° C, Pitzer's Parameterisation," Chemical Geology 140, (1997), 155-165.

Zhou et al., "Effect of Sodium Chloride on Gelatinization of Silicic Acid and the Formation of Novel Polysilicic Acid Crystals," Journal of Non-Crystalline Solids, 353 (2007), 2774-2778.

Nour et al., "Spectroscopic Evidence of Silica-Lignin Complexes: Implications for Treatment of Non-Wood Pulp Wastewater," Water Science and Technology, vol. 50, No. 3, pp. 157-166, 2004.

Chen et al., "Influence of Catechin on Precipitation of Aluminum Hydroxide," ScienceDirect Geoderma 152 (2009), 296-300.

Ohman et al., "Equilibrium and Structural Studies of Silicon (IV) and Aluminum (III) in Aqueous Solution. 28. Formation of Soluble Silicic Acid-Ligand Complexes as Studied by Potentiometric and Solubility Measurements," Department of Inorganic Chemistry, University of Umea, S-901 87, pp. 335-341, 1990.

Pokrovski et al., "Experimental Study of the Complexation of Silicon and Germanium with Aqueous Organic Species: Implications for Germanium and Silicon Transport and Ge/Si Ratio in Natural Waters," Geochimica et Cosmochimica Acta, vol. 62, No. 21/22, pp. 3413-3428, 1998.

Dhar et al., "Six-Coordinate Silicon (IV). The Hydrolysis and Racemization of the Tris-(Acetylacetonato)-Silicon (IV) Cation," Department of Chemistry, Wayne State University, vol. 81, 1959.

Gorrepati et al., "Silica Precipitation in Acidic Solutions: Mechanism, pH Effect, and Salt Effect," Langmuir, American Chemical Society, 2010.

Sedeh et al., "Equilibrium and Structural Studies of Silicon (IV) and Aluminum (III) in Aqueous Solution. 30. Aqueous Complexation Between Silicic Acid and Some Ortho-Di and Triphenolic Compounds," Department of Inorganic Chemistry, University of Umea, S-901 87, pp. 933-940, 1992.

Gorrepati, "Silica Precipitation from Analcime Dissolution," A Dissertation Submitted in Partial Fulfillment of the Requirements for the Degree of Doctor of Philosophy (Chemical Engineering) in the University of Michigan, 2009.

Office Action for U.S. Appl. No. 11/998,733 dated Mar. 29, 2010.

Sunco Technical Data Sheet of Polyacrylate Thinner, Undated.

Kefeli et al. "Synthesis and Polymerization of Polyacrylic Esters", Journal of Polymer Science, vol. 52, pp. 169-177, 1961.

International Search Report and Written Opinion for PCT/GB2009/002424 dated May 18, 2010.

International Search Report and Written Opinion for PCT/GB2009/002422 dated Jan. 21, 2010.

International Preliminary Report on Patentabiilty for PCT/GB2009/002415 dated Apr. 21, 2011.

Protex-All™ Scale Inhibitor brochure, Jan. 2008.

Scalechek® LP-55 Scale Inhibitor brochure, Jan. 2008.

Communication for International Patent Application No. PCT/GB2009/002424 dated Mar. 3, 2010.

"Fracture-Related Diagenesis May Impact Conductivity," J. Weaver, M. Parker, D. van Batenburg, and P. Nguyen, Halliburton, 2006 SPE International Symposium and Exhibition on Formation Damage Control held in Lafayette, LA Feb. 15-17, 2006; revised manuscript received Jan. 16, 2007.

Weaver et al., E & P Formation Mineralogy, Proppant Characteristics Drive Conductivity; Apr. 22, 2009; XP-002557372.

International Search Report and Written Opinion for PCT/GB2009/002415 dated Dec. 22, 2009.

International Search Report for Patent Application No. PCT/GB2009/002424 dated Jul. 1, 2010.

U.S. Appl. No. 12/573,999, filed Oct. 6, 2009, Nguyen et al.

U.S. Appl. No. 12/574,037, filed Oct. 6, 2009, Reyes et al.

U.S. Appl. No. 12/574,054, filed Oct. 6, 2009, Reyes et al.

SPE 51049-MS "Enhancing Unconventional Gas Development Economics Through Proppant Surface Modification," M.E. Blauch, Halliburton, W.K. Morrison, CMS Nomeco, J.G. Wilkinson, Ward Lake Energy, J. Minthorn, and J. Terracina, Halliburton, 1998 SPE Eastern Regional Meeting held in Pittsburgh, Pennsylvania, Nov. 9-11, 1998.

SPE 94666-MS "Sustaining Fracture Conductivity," J.D. Weaver, P.D. Nguyen, M.A. Parker, and D. van Batenburg, Halliburton, SPE European Formation Damage Conference held in Scheveningen, The Netherlands, May 25-27, 2005.

SPE 97659-MS "Controlling Formation Fines at Their Sources to Maintain Well Productivity," P.D. Nguyen, J.D. Weaver, R.D. Rickman, R.G. Dusterhoft, and M.A. Parker, Halliburton, SPE International Improved Oil Recovery Conference in Asia Pacific held in Kuala Lumpur, Malaysia, Dec. 5-6, 2005.

SPE 97659-PA "Controlling Formation Fines at Their Sources to Maintain Well Productivity," P.D. Nguyen, J.D. Weaver, R.D. Rickman, R.G. Dusterhoft, and M.A. Parker, Halliburton, SPE Intl Improved Oil Recovery Conf. in Asia Pacific, Kuala Lumpur, Malaysia, Dec. 5-6, 2005.

SPE 98236-MS "Sustaining Conductivity," J.D. Weaver, D.W. van Batenburg, M.A. Parker, and P.D. Nguyen, Halliburton, 2006 SPE International Symposium and Exhibition on Formation Damage Control held in Lafayette, LA Feb. 15-17, 2006.

SPE 98236-PA "Fracture-Related Diagenesis May Impact Conductivity," J. Weaver, M. Parker, D. van Batenburg, and P. Nguyen, Halliburton, 2006 SPE International Symposium and Exhibition on Formation Damage Control held in Lafayette, LA Feb. 15-17, 2006.

SPE 106815-MS "Surface Reactive Fluid's Effect on Shale," Bill Grieser, Halliburton; Bill Wheaton, Devon Energy Production Co., LP; Bill Magness, Williams Energy Services Co.; and Matt Blauch and Ray Loghry, Halliburton, 2007 SPE Production and Operations Symposium held in Oklahoma City, Oklahoma, U.S.A., Mar. 31-Apr. 3, 2007.

SPE 118174-MS "Fracture-Conductivity Loss Due to Geochemical Interactions Between Manmade Proppants and Formations," J. Weaver, R. Rickman, H. Luo, Halliburton, 2008 SPE Eastern Regional/AAPG Eastern Section Joint Meeting in Pittsburg, PA, Oct. 11-15, 2008.

SPE 118175-MS "Prevention of Geochemical Scaling in Hydraulically Created Fractures: Laboratory and Field Studies," P. Nguyen, J. Weaver and R. Rickman, Halliburton, 2008 SPE Eastern Regional/AAPG Eastern Section Joint Meeting in Pittsburg, PA, Oct. 11-15, 2008.

SPE 121465-MS "A Study of Proppant Formation Reactions," J. Weaver, R. Rickman, H. Luo, R. Loghry, Halliburton, 2009 SPE International Symposium on Oilfield Chemistry held in The Woodlands, TX, Apr. 20-22, 2009.

International Search Report and Written Opinion for PCT/GB2009/002423 dated Jan. 21, 2010.

Ali, Syed A.; Sandstone Diagenesis, Applications to Hydrocarbon Exploration and Production; Gulf Science & Technology Company; Pittsburgh, PA; Geology & Interpertation Department; Department Report No. 4231R006; Dec. 1981.

* cited by examiner

US 8,119,576 B2

CERAMIC COATED PARTICULATES

CROSS-REFERENCE TO RELATED APPLICATIONS

This application claims benefit of U.S. Provisional Patent Application Ser. Nos. 61/104,610, 61/104,620, 61/104,624, and 61/104,629, each filed Oct. 10, 2008, each of which is herein incorporated by reference.

This application is related to U.S. patent application Ser. No. 12/573,999 entitled "Prevention of Water Intrusion into Particulates," by Nguyen et al., U.S. patent application Ser. No. 12/574,037, entitled "Additives to Suppress Silica Scale Build-up," by Reyes et al., and U.S. patent application Ser. No. 12/574,054, entitled "Geochemical Control of Fracturing Fluids," by Reyes et al., filed on the same day herewith, which are hereby incorporated by reference in their entirety.

BACKGROUND

The present disclosure relates to treatments and compounds useful in subterranean formations, and, at least in some embodiments, to treatments and compounds utilizing ceramic coated particulates.

In the production of fluids, such as hydrocarbons or water, from a subterranean formation, the subterranean formation should be sufficiently conductive to permit the flow of desirable fluids to a well bore penetrating the formation. Among others, hydraulic fracturing may be a useful treatment for increasing the conductivity of a subterranean formation. Hydraulic fracturing operations generally may involve pumping a treatment fluid (e.g., a fracturing fluid or a "pad fluid") into a well bore that penetrates a subterranean formation at a sufficient hydraulic pressure to create or enhance one or more pathways, or "fractures," in the subterranean formation. Enhancing a fracture generally involves extending or enlarging a natural or pre-existing fracture in the formation. These fractures generally increase the permeability of that portion of the formation. The treatment fluid may comprise particulates, including proppant particulates that are deposited in the resultant fractures. The particulates are thought to help prevent the fractures from fully closing upon release of the hydraulic pressure, forming conductive channels through which fluid may flow between the formation and the well bore.

It is generally believed that the surfaces of particulates generally comprise minerals, which may react with other substances (e.g., water, minerals, treatment fluids, and the like) that reside in the subterranean formation in chemical reactions caused, at least in part, by conditions created by mechanical stresses on those minerals (e.g., fracturing of the mineral surfaces or the compaction of particulates). These reactions are herein referred to as "stress-activated reactions" or "stress-activated reactivity." One type of these stress-activated reactions may be diageneous reactions. As used herein, the terms "diageneous reactions," "diageneous reactivity," and "diagenesis" include chemical and/or physical processes that, in the presence of water, move a portion of the mineral in a particulate and/or convert a portion of the mineral in a particulate into some other form. A mineral that has been so moved or converted is herein referred to as a "diageneous product" or "diagenic product." Any particulate comprising a mineral may be susceptible to these diageneous reactions, including natural silicate minerals (e.g., quartz), man-made silicates and glass materials, metal oxide minerals (both natural and man-made), and the like.

Two of the principal mechanisms that diagenesis reactions are thought to involve are "pressure dissolution" and "precipitation processes." Where two water-wetted mineral surfaces are in contact with each other at a point under strain, the localized mineral solubility near that point may increase, causing the minerals to dissolve. Minerals in solution may diffuse through the water film outside of the region where the mineral surfaces are in contact (e.g., the pore spaces of a particulate pack), where they may precipitate out of solution. The dissolution and precipitation of minerals in the course of these reactions may reduce the conductivity of a particulate pack, inter alia, by clogging the pore spaces in the particulate pack with mineral precipitate and/or collapsing the pore spaces by dissolving solid mineral in the "walls" of those pore spaces. In other instances, minerals on the surface of a particulate may exhibit a tendency to react with substances in the reservoir, formation, and/or treatment fluids that are in contact with the particulates, such as water, gelling agents (e.g., polysaccharides, biopolymers, etc.), and other substances commonly found in these fluids. Molecules from such substances may become anchored to the mineral surface of the particulate. These types of reactivity may further decrease the conductivity of a subterranean formation, inter alia, through the obstruction of conductive fractures in the formation by any molecules that have become anchored to the particulates resident within those fractures. Both types of reactions may generally require the presence of a fluid, such as water, to occur to any significant extent.

SUMMARY

The present disclosure relates to treatments and compounds useful in subterranean formations, and, at least in some embodiments, to treatments and compounds utilizing ceramic coated particulates.

One embodiment of the present invention provides a method. The method comprises providing a plurality of particulates, wherein at least a portion of the particulates are coated with a ceramic, and wherein the ceramic coating is of subatomic thickness. The method further comprises introducing the plurality of particulates into a subterranean formation. The method further comprises allowing an aqueous fluid to flow through the plurality of particulates. The method further comprises allowing the ceramic to impede aqueous fluid interactions between the aqueous fluid and the plurality of particulates.

Another embodiment of the invention provides another method. The method comprises providing particulate pack, wherein at least a portion of the particulate pack is coated with a ceramic, and wherein the ceramic coating is of subatomic thickness. The method further comprises allowing an aqueous fluid to flow through the particulate pack. The method further comprises allowing the ceramic to impede aqueous fluid interactions between the aqueous fluid and the particulate pack.

Yet another embodiment of the invention provides a composition. The composition comprises a particulate pack and a ceramic coating on at least a portion of the particulate pack, wherein the ceramic coating is of subatomic thickness, and wherein the ceramic coating is capable of impeding aqueous fluid interactions between an aqueous fluid and the particulate pack.

The features and advantages of the present invention will be apparent to those skilled in the art. While numerous changes may be made by those skilled in the art, such changes are within the spirit of the invention.

DESCRIPTION OF PREFERRED EMBODIMENTS

The present disclosure relates to treatments and compounds useful in subterranean formations, and, at least in some embodiments, to treatments and compounds utilizing ceramic coated particulates.

The term "coating" as used herein refers to at least a partial coating of some or all of the particulates. Neither complete nor substantial coverage of the particulates or mix of particulates is implied by the term "coating." Rather, a particulate may be coated if it has, for example, at least a partial coating.

The term "derivative" is defined herein to include any compound that is made from one of the listed compounds, for example, by replacing one atom in the listed compound with another atom or group of atoms, rearranging two or more atoms in the listed compound, ionizing one of the listed compounds, or creating a salt of one of the listed compounds. A derivative of a material may include, but is not limited to, a compound composition based on a plurality of base materials, a composite material, or an aggregated material of various compositions.

As used herein, the terms "diageneous reactions," "diageneous reactivity," and "diagenesis" include chemical and physical processes that, in the presence of water, move a mineral and/or convert a mineral into some other form. Examples of such minerals include, but are not limited to, oxides or hydroxides of zirconium, magnesium, aluminum, titanium, calcium, strontium, barium, radium, zinc, cadmium, boron, gallium, iron, or any other element suitable for forming a diagenic product. Such minerals may be found in a particulate, in a formation, and/or introduced into a formation as "diagenesis source material." A mineral that has been so moved or converted is herein referred to as a "diageneous product" or "diagenic product."

As used herein, the term "aqueous fluid interaction" includes a variety of possible interactions between an aqueous fluid and a particulate. Such interactions may include infiltration of the aqueous fluid into the particulate, for example, by infiltrating pores, voids, crevices, cracks, and/or channels at or near the surface of the particulate. Such interactions may also include diagenesis.

As used herein, the term "diffusion barrier" includes any sort of material, including a coating, on or proximate to a particle that impedes and/or prevents aqueous fluid interaction with the particle. For example, some diffusion barriers fill or coat pores, voids, crevices, cracks, or channels at or near the particle's surface to impede and/or prevent infiltration by the aqueous fluid. As another example, some diffusion barriers impede and/or prevent diagenesis.

As used herein, the term "diagenic protective materials" refers to one or more diagenic products that may be selectively promoted in order to form a diffusion barrier.

As used herein, the term "filler" or "filler material" means a particulate material that is capable of fitting within a pore, void, crevice, crack, or channel at or near the surface of a particulate or on surfaces within the porous matrix of the individual particulates.

As used herein, the term "relatively low molecular weight" refers to a molecular weight that would encompass monomers and short-chain polymers having physical dimensions from a few angstroms to several hundred nanometers.

As used herein, a "monolayer" refers to a coating of a material approximately one unit thick. For chemicals, this may mean a coating as thin as one molecule, and for particulate compositions, it may mean a coating one particulate grain deep.

As used herein, the terms "pores," "voids," "crevices," "cracks," and "channels" refer to features at or near the surface of a particulate. Any given particulate may have one or more pores, voids, crevices, cracks, or channels, or may be free of such features. One or more such features may be generally referred to as "surface features." The use of the terms in conjunction is in no way intended to indicate that all three must be present simultaneously, or at all, in order for the teachings of the present disclosure to apply.

As used herein, the terms "particle," "particulate," "proppant particulate," and "gravel" are all used to refer to either a single particle or a plurality of particles which may be used for supporting a fracture in an underground formation, for forming a proppant pack, or for use in forming a gravel pack. Such particles may be disposed in a subterranean formation, including in spaces in the rock itself, fractures within the rock, and/or a well bore penetrating the subterranean formation.

As used herein, the term "pack" or "particulate pack" refers to a collection of particulates within an enclosed volume, wherein the particulates may be juxtaposed and/or in contact with one another, and wherein pore spaces may be disposed between the particulates. Examples of "packs" may include "proppant packs," which may refer to a collection of proppant particulates within a fracture, and/or "gravel packs," which may refer to a grouping of particulates that are packed sufficiently close together so as to prevent the passage of certain materials through the pack.

The term "on-the-fly" is used herein to indicate that one flowing stream comprising particulates is introduced into another flowing stream comprising a hydrophobic coating agent so that the streams are combined and mixed to flow as a single stream. In some instances, the streams may be combined to flow as a single stream as part of an on-going treatment at the job site. Such mixing can also be described as "real-time" mixing.

As used herein, the term "silica scale control additive" may be any product capable of suppressing silica scale build-up by increasing the solubility of silica in solution, inhibiting silica polymer chain propagation, and/or decreasing the size or quantity of any silica scale created in a solution.

The term "gel," as used herein and its derivatives refer to a viscoelastic or semi-solid, jelly-like state assumed by some colloidal dispersions.

As used herein, the term "ceramic" is intended to refer to an inorganic, nonmetallic material, typically crystalline in nature, though it could be amorphous as well. Ceramics generally may be compounds formed between metallic and nonmetallic elements, such as, for example, aluminum and oxygen (e.g., alumina—$Al_2O_3$), calcium and oxygen (e.g., calcia—CaO), silicon and oxygen (e.g., silica—$SiO_2$) and other analogous oxides, nitrides, borides, sulfides, and carbides.

If there is any conflict in the usages of a word or term in this specification and one or more patent or other documents that may be incorporated herein by reference, the definitions that are consistent with this specification should be adopted for the purposes of understanding this invention.

There are many advantages of the present invention, only some of which are mentioned here. One advantage of the present invention may be the protection of particulates from degradation when in the presence of an aqueous fluid. When placed in a subterranean formation—including in the rock itself, fractures within the rock, and/or a well bore penetrating the subterranean formation—the particulates may undergo diagenic reactions with the aqueous fluids. Such reactions may produce diagenic products that may cause the particulates to break down or result in plugging of the interstitial spaces in a particulate pack. In an embodiment, the particulates may be coated with a ceramic layer of material in order to impede aqueous fluid interactions between aqueous fluids and the particulates, thereby limiting the diagenesis reactions and maintaining the permeability of the particulate packs.

Protecting particulates from degradation may be achieved in several ways. In some embodiments, material may be coated on the particulates which may make the particulates less reactive in a subterranean formation environment. A variety of coatings may be used, and appropriate manufacturing methods for coating the particulates may be selected depending on the types of coating materials utilized.

The particulates that may be used in embodiments of the present invention include any proppant or gravel particulates that may be used in a subterranean application. Suitable particulates may include sand, sintered bauxite, silica alumina, glass beads, etc. Other suitable particulates include, but are not limited to, sand, bauxite, garnets, fumed silica, ceramic materials, glass materials, polymer materials, polytetrafluoroethylene materials, nut shell pieces, seed shell pieces, fruit pit pieces, wood, composite particulates, proppant particulates, degradable particulates, coated particulates, gravel, and combinations thereof. Suitable composite materials may comprise a binder and a particulate material wherein suitable particulate materials may include silica, alumina, garnets, fumed carbon, carbon black, graphite, mica, titanium dioxide, meta-silicate, calcium silicate, kaolin, talc, zirconia, boron, fly ash, hollow glass microspheres, solid glass, and combinations thereof. In certain embodiments, the particles may comprise common sand. In some embodiments, a derivative of one or more of the particulate materials may also be used. Derivatives may include materials such as compounds, composite materials, and aggregated materials of various compositions. In some embodiments of the present invention, some or all of the particulates may be comprised of a diagenesis source material. In this embodiment, the particulates may comprise oxides or hydroxides of zirconium, magnesium, aluminum, titanium, calcium, strontium, barium, radium, zinc, cadmium, boron, gallium, iron, or any other element suitable for forming a diagenic product. Suitable particulates may take any shape including, but not limited to, the physical shape of platelets, shavings, flakes, ribbons, rods, strips, spheres, spheroids, ellipsoids, toroids, pellets, or tablets. Although a variety of particulate sizes may be useful in the present invention, in certain embodiments, particulate sizes may range from about 200 mesh to about 8 mesh.

Embodiments of particulates of the present invention may contain pores, voids, crevices, cracks, or channels at or near the surface. For example, SEM micrographs at high magnification may show that the surfaces of particles, such as particulates made from bauxite, may be laden with pores, voids, crevices, cracks, and channels. Without being limited by theory, it is believed that these pores, voids, crevices, cracks, or channels at or near the particulate surface may provide a direct path to allow a detrimental interaction between aqueous fluids and the particles that may lead to degradation of the particles under formation pressure and temperature.

In some embodiments, the particulates may be treated or coated with one or more suitable substances. Generally, the particulates may be treated or coated with any substance which is suitable for traditional particulate treatments. In certain embodiments, the particulates may be coated so as to impede the intrusion of water into the particulates. For example, the particulates may be coated and/or used as discussed in "Prevention of Water Intrusion Into Particulates" by Nguyen et al., U.S. patent application Ser. No. 12/573,999, "Additives to Suppress Silica Scale Build-up" by Reyes et al., U.S. patent application Ser. No. 12/574,037, and/or "Geochemical Control of Fracturing Fluids" by Reyes et al., U.S. patent application Ser. No. 12/574,054, each filed on the same day herewith, and the entire disclosures of which are hereby incorporated by reference in their entirety. In an embodiment, a portion of the particulates may be coated so as to limit their diagenic reactivity while others may remain uncoated so as to provide a reaction site for the diagenesis source material.

In an embodiment, the particulates may be coated with a ceramic. The ceramic may impede aqueous fluid interactions between the particulates and aqueous fluids, including aqueous treatment and/or formation fluids. In an embodiment, an appropriate ceramic may include silicon carbide, silicon nitride, boron carbon, boron carbide, diamond-like-carbon, titanium carbide, aluminum nitride, chromium carbide, mixed carbide, nitride, and carbonitride alloys, and cubic boron nitride. In an embodiment, a plurality of ceramics may be used in conjunction to combine advantageous effects. In an embodiment, a derivative of one or more ceramic materials may also be used. Derivatives may include materials such as compounds, composite materials, and aggregated compositions of various ceramic materials.

One of ordinary skill in the art, with the benefit of this disclosure, will be able to determine which ceramic or ceramics should be coated on a particulate based on, for example, formation chemistry, formation conditions (e.g., temperature, pressure, etc.), particulate composition, resource availability, costs and logistics considerations, and any physical limitations inherent in the coating process. In an embodiment, the coating layer may vary in thickness depending on the subterranean operation requirements. In some embodiments, the ceramic may be a monolayer thick, while in other embodiments, a thicker layer may be desired. In particular, some embodiments may provide a very thin ceramic layer of subatomic thickness. In such embodiments, the ceramic thickness may be between about 100 nanometers and about 50,000 nanometers. The resulting coated particulate may have ceramic from between about 0.1% to about 10% by weight of the particulate. In another embodiment providing a ceramic layer of subatomic thickness, the ceramic thickness may be between about 100 nanometers and about 500 nanometers. The resulting coated particulate may have ceramic from between about 0.5% to about 2% by weight of the particulate.

In some embodiments, a variety of methods may be useful in coating a ceramic on particulates. Any method capable of coating a ceramic on a particulate may be used. In an embodiment, chemical vapor deposition, physical vapor deposition, dip coating, spray pyrolysis, sputtering, sintering, and chemical vapor infiltration may be used to ceramic onto a particulate. For any methods requiring a chemical reaction to form a ceramic coating (e.g., chemical vapor deposition or spray pyrolysis), any appropriate precursors may be determined by one skilled in the arts. For example, single source precursors for forming silicon carbides may include, but are not limited to, polycarbosilanes, polysilazanes, silylenes, perfluoroalkylsilanes or functionalized silylenes, and mixtures such as alkylchlorosilanes, ethylene, and hydrogen for instance. One skilled in the art will be able to determine the appropriate coating technique, reaction conditions, and precursors, if needed, based upon the type of ceramic desired and the particulate composition. For embodiments in which more than one layer of the ceramic is coated on the particulates, the same or different coating methods may be used. Due to the conditions generally required to form a ceramic coating on a particulate, the particulates may generally be coated in a manufacturing process prior to being shipped to the well site. In some embodiments, the particulates may be coated at the well site and/or on the fly.

One embodiment of the present invention provides a method. The method comprises providing a plurality of particulates, wherein at least a portion of the particulates are coated with a ceramic, and wherein the ceramic coating is of subatomic thickness. The method further comprises introducing the plurality of particulates into a subterranean formation. The method further comprises allowing an aqueous fluid to flow through the plurality of particulates. The method further comprises allowing the ceramic to impede aqueous fluid interactions between the aqueous fluid and the plurality of particulates. In some embodiments, this method may be useful in the recovery of fluids from the subterranean formation. The fluids being recovered may be a fluid previously introduced into the subterranean formation, an aqueous reservoir and/or formation fluid, a hydrocarbon fluid, or a combination thereof. By way of example, a fluid comprising a plurality of particulates coated with a ceramic may be introduced into a subterranean formation at or above a pressure sufficient to create or enhance one or more fractures in the subterranean formation.

Another embodiment of the invention provides another method. The method comprises providing particulate pack, wherein at least a portion of the particulate pack is coated with a ceramic, and wherein the ceramic coating is of subatomic thickness. The method further comprises allowing an aqueous fluid to flow through the particulate pack. The method further comprises allowing the ceramic to impede aqueous fluid interactions between the aqueous fluid and the particulate pack. In some embodiments, this method may be useful in the recovery of fluids from the subterranean formation. The fluids being recovered may be a fluid previously introduced into the subterranean formation, an aqueous reservoir and/or formation fluid, a hydrocarbon fluid, or a combination thereof.

Yet another embodiment of the invention provides a composition. The composition comprises a particulate pack and a ceramic coating on at least a portion of the particulate pack, wherein the ceramic coating is of subatomic thickness, and wherein the ceramic coating is capable of impeding aqueous fluid interactions between an aqueous fluid and the particulate pack. In some embodiments, this method may be useful in preparation of particulates for subterranean treatments and/or usage of particulates in subterranean treatments.

In order to quantify the mechanical strength of the particulates and permeability of the particulate pack, both before and after exposure to formation conditions and fluids, several test procedures may be utilized to determine various particulate properties. The first test method studies temperature-promoted diagenesis of a particulate pack by exposing a particulate pack to a flowing solution of simulated formation fluid at an approximate formation temperature. The second procedure studies stress/temperature-promoted diagenic growth through exposure of a particulate pack to a static flow environment under simulated formation pressures and temperatures. The mechanical strength of individual particulates may be measured before and after the test procedures to determine the percentage of particulate strength lost due to exposure to formation temperature or pressure. Alternatively, the permeability of the particulate pack may be measured before and after the temperature-promoted diagenesis test in order to determine a retained permeability value for the particulate pack. As would be understood by one of ordinary skill in the art with the benefit of this disclosure, expected subterranean formation conditions (e.g., temperature, pressure, formation fluid composition) for a selected subterranean formation will determine the appropriate formation conditions for test procedures.

In the temperature-promoted diagenesis test procedure, deionized water may first be heated to a test temperature of between about 200 degrees Fahrenheit (° F.) and about 600° F. by passing it through a heat exchanger coil. Simulated formation fluid may be formed by passing the deionized water through multiple packs of crushed formation material arranged in series. The number of formation packs required for the test may vary such that the simulated formation fluid leaving the last pack may be in equilibrium with the crushed formation material. Through experimentation, the typical number of formation packs may generally be between about 1 and about 10. Crushed formation material may be screened to remove fines and an approximately 8/35 mesh fraction may be used in the formation packs.

In an embodiment, once a simulated formation fluid in equilibrium with the crushed formation material is obtained, the simulated formation fluid may be directed to a column containing a particulate pack. The temperature in the particulate pack may be maintained at an approximate formation temperature between about 200° F. and about 600° F., which approximately corresponds to the temperature of the deionized water first entering the system. A flow rate of simulated formation fluid may be maintained at approximately 1 milliliter per minute during the test.

The flow test may be maintained for between about 10 to about 200 days, and in an embodiment, for at least about 20 days. After this time, the particulate pack may be disassembled in order to test the mechanical properties of individual particles, as discussed in more detail below. For example, surface and compositional analysis may be made after disassembly to determine what types of materials are being formed under the simulated formation conditions. A permeability test may also be performed at this time. In this test, the permeability of the particulate packs may be measured at room temperature prior disassembly of the particulate pack. The measured permeability of the pack may then be compared with an initial permeability measurement made of the pack at room temperature before the pack is placed in the testing apparatus. Comparing the initial permeability measurement with the permeability measurement obtained after the pack is subjected to the test conditions may allow for a retained permeability to be calculated.

The stress/temperature-promoted diagenesis test method may involve the testing of the particulate pack under static flow conditions at approximate formation pressures and temperatures. In this method, a pack of particulates may be loaded in a test cell and filled with a salt solution. The test cell may be loaded from between about 0.5 pounds per square foot ($lb/ft^2$) of particulates to about 3.0 $lb/ft^2$ of particluates. In an embodiment, an approximately 2% KCl solution may be used as the fluid medium. Formation wafers, either manufactured from formation core material or from rock outcrop material, may be placed above and below the particulate pack in the test column. The system may then be shut in and placed under simulated formation pressure and heated to approximate formation temperatures. In an embodiment of this method, the temperature may be maintained at between about 100° F. and about 550° F. In another embodiment, the temperature may be maintained at between about 100° F. and about 350° F. The pressure may be maintained at between about 2,000 psi and about 10,000 psi. In another embodiment, the pressure may be maintained at between about 5,000 psi and about 8,000 psi.

In an embodiment, the test may be conducted for between about 1 to about 50 weeks, and in another embodiment, the test may be conducted for at least about 4 weeks (about 28 days).

Upon completion of the stress/temperature-promoted diagenesis test, the test cell may be disassembled and the particulate pack removed for testing. As with the flow test method, additional tests may also be performed at this time. For example, surface and compositional analysis may be made after disassembly to determine what types of materials are being formed under the simulated formation conditions. Alternatively, the resulting interstitial fluid may be analyzed to determine the relative solubility of the particulates under formation conditions.

Changes in the mechanical properties of the particulates obtained from either the stress/temperature-promoted diagenesis test or the temperature-promoted diagenesis test may be determined using a single-grain crush-strength analysis. The analysis may utilize a Weibull statistical analysis procedure based on a plurality of particulate crush samples. The crush test may be based on a uni-axial compressive point loading of a particle. Under a compressive loading in the uni-axial direction, a spherical particle may be under tension in directions perpendicular to the loading with a tensile stress, $\sigma$, calculated by $$\sigma = \frac{2.8F}{\pi d^2}$$

where d is the diameter of each particle and F is the load at failure.

A Weibull analysis may include a statistically significant number of crush samples, which may range from about 10 to about 50 individual crush samples, or from about 20 to about 40 individual crush samples. In an embodiment, a sample size of between about 25 and about 30 individual crush samples of particulates may be used in the analysis. All of the strength data points may then be sorted from low to high as $\sigma_1 < \sigma_2 < \sigma_3 < \ldots < \sigma_N$, where N represents the total number of samples. A probability of failure may be calculated from the equation:

$$P_f = \left(\frac{\# - 0.5}{N}\right)$$

where, as before, N is the total number of samples, for example about 30 samples, and # is the index number for the sorted strength values (e.g., 1 through N). A linear plot may be obtained by plotting $$\ln\left(\ln\left(\frac{1}{1-P_f}\right)\right) \text{ vs } \ln(\sigma)$$

A Weibull distribution may be found by linear fitting and generating an equation:

$$\ln\left(\ln\left(\frac{1}{1-P_f}\right)\right) = m\ln\left(\frac{\sigma}{\sigma_0}\right)$$

where m is the Weibull modulus and $\sigma_0$ is the characteristic strength. The strength will tend to increase along with the reliability of the strength calculation when the $\sigma_0$ and m values increase. The characteristic strength changes in the particulates may then be determined. By comparing the characteristic strength of the particulates prior to exposure to the simulated formation fluid with the characteristic strength of the particulates after exposure to the simulated formation fluid, a retained strength value may be calculated from the equation:

$$\text{Retained } \sigma_0 = \left(\frac{\text{Exposed } \sigma_0}{\text{Unexposed } \sigma_0}\right)$$

where, Exposed $\sigma_0$ is the characteristic strength of the particles after exposure to the simulated formation fluid, and Unexposed $\sigma_0$ is the characteristic strength of the particles prior to exposure. Similarly, a retained permeability may be calculated by dividing the permeability measured at the end of the temperature-promoted diagenesis test with the permeability measured at the beginning.

In an embodiment, a single set of test conditions may be utilized for comparison of different sets of sets of particles comprising diffusion barriers and/or filler materials. The retained strength value is defined to be measured by the stress/temperature-promoted diagenesis test. In this method, a pack of particulates is loaded in a test column and filled with a salt solution comprising an approximately 2% KCl solution. The test cell is loaded with about 2 lb/ft$^2$ of particulates. Formation wafers are placed above and below the particulates in the test cell. The system is then shut in and placed under a pressure that is approximately equal to the pressure expected in the formation in which the particulates are expected to be placed. The temperature may be maintained at a temperature that is approximately equal to the formation temperature where the particulates are expected to be placed. For example, the system may be placed under simulated formation pressure of about 9000 psi and temperature of about 250° F. These conditions are then maintained for about 28 days.

Upon completion of the stress/temperature-promoted diagenesis test, the test cell is disassembled and the particulate matrix removed for testing. Changes in the mechanical properties of the particulates are obtained using particulates tested using the stress/temperature-promoted diagenesis test. The analysis utilizes a Weibull statistical analysis procedure based on a plurality of particulate crush samples, as discussed above. A single analysis includes a statistically significant number of samples, which may be between about 20 and about 40 samples, e.g., approximately 30 crushed samples of individual particles. However, in some instances, the sample size may vary such that the actual number of samples is smaller or larger in order to obtain a statistically significant number of samples. The characteristic strength changes in the particulates may then be determined. By comparing the characteristic strength of the particulates prior to exposure to the simulated formation fluid with the characteristic strength of the particulates after exposure to the simulated formation fluid, a retained strength value is calculated from the equation:

$$\text{Retained } \sigma_0 = \left(\frac{\text{Exposed } \sigma_0}{\text{Unexposed } \sigma_0}\right)$$

where, Exposed $\sigma_0$ is the characteristic strength of the particles after exposure to the simulated formation fluid, and Unexposed $\sigma_0$ is the characteristic strength of the particles prior to exposure.

Similarly, the retained permeability value of the particulate pack is defined to be measured by the temperature-promoted diagenesis test. In the temperature-promoted diagenesis test procedure, an initial permeability measurement is made of a particulate pack while the particulate pack is at room temperature. Deionized water is then heated to a test temperature of approximately 500° F. by passing it through a heat exchanger coil. Lower test temperatures may also be used depending on the specific particulate material and coating used. For example, one of ordinary skill in the art may determine that a lower test temperature is required in order to avoid thermal decomposition of the particulates, the diffusion barrier, or the filler material. Simulated formation fluid is formed by passing the deionized water through multiple packs of crushed formation material arranged in series. The number of formation packs required for the test may vary such that the simulated formation fluid leaving the last pack is in equilibrium with the crushed formation material at the flow rate used during the test of approximately 1 milliliter per minute. The typical number of formation packs is generally between about 2 and about 5. Crushed formation material is screened and an approximately 8/35 mesh fraction is used in the formation packs. The formation material is obtained by crushing a core withdrawn from a specific well during drilling or from dill cuttings obtained while a well is being drilled through a zone of interest.

The simulated formation fluid is then directed to a column containing a particulate pack. The temperature in the particulate pack is maintained at a temperature of about 500° F. A lower test temperature may be used depending on the specific particulate material and coating material used. For example, one of ordinary skill in the art may determine that a lower test temperature is required in order to avoid thermal decomposition of the particulates, the diffusion barrier, or the filler. A flow rate of simulated formation fluid is maintained at approximately 1 milliliter per minute during the test. The flow test is maintained for about 30 days. After this time, permeability of the particulate pack is measured prior to disassembly and after the particulate pack has been allowed to cool to room temperature, allowing for a retained permeability to be calculated from the equation:

$$\text{Retained Permeability} = \left(\frac{\text{Exposed Permeability}}{\text{Unexposed Permeability}}\right)$$

where, Exposed Permeability is the permeability of the particles after exposure to the simulated formation fluid, and Unexposed Permeability is the permeability of the particles prior to exposure.

Particulates prepared and tested according to the methods of the current invention using the characteristic conditions of the embodiment may exhibit a retained strength value of greater than about 20%. Alternatively, the particulates may exhibit a retained strength value of greater than about 60%. In still another embodiment, the particulates may exhibit a retained strength value of greater than about 80%. In yet another embodiment, the particulates may exhibit a retained strength value of greater than about 90%. In an embodiment, the particulates used to form a pack may be characterized by a retained permeability value of at least about 40%. In another embodiment, the particulates may be characterized by a retained permeability of at least about 60%. In still another embodiment, the particulates may be characterized by a retained permeability of at least about 80%. In some embodiments, the retained permeability may be at least about 99%.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

What is claimed is:

1. A method comprising:
   providing a plurality of particulates, wherein at least a portion of the particulates are coated with a ceramic coating ranging between about 100 nm and about 500 nm in thickness;
   introducing the plurality of particulates into a subterranean formation;
   allowing an aqueous fluid to flow through the plurality of particulates; and
   allowing the ceramic coating to impede aqueous fluid interactions between the aqueous fluid and the plurality of particulates.

2. The method of claim 1, wherein the ceramic coating is present on the particulates in an amount of between about 0.1% to about 10% by weight of the particulates.

3. The method of claim 1, wherein the ceramic coating comprises at least one substance selected from the group consisting of silicon carbide, silicon nitride, boron carbon, boron carbide, diamond-like-carbon, titanium carbide, aluminum nitride, chromium carbide, a mixed carbide, a nitride and carbonitride alloy, cubic boron nitride, any combination thereof, and any derivative thereof.

4. The method of claim 1, wherein some of the particulates are coated with a second ceramic to form a plurality of ceramic layers.

5. The method of claim 1 wherein the plurality of particulates comprise at least one substance selected from the group consisting of: a sand, a sintered bauxite, a silica alumina, a glass bead, a bauxite, a fumed silica, a ceramic material, a glass material, a polymer material, a polytetrafluoroethylene material, a composite particulate, a coated particulate, a degradable particulate, a proppant, a gravel, any combination thereof, and any derivative thereof.

6. The method of claim 1, wherein at least a portion of the plurality of particulates form a pack in a portion of the subterranean formation;
   wherein the pack has a retained permeability of about 40% or more as determined using a temperature-promoted diagenesis test using formation conditions expected for the subterranean formation.

7. The method of claim 1, wherein the particulates have a retained strength of about 30% or more as determined using a stress/temperature-promoted diagenesis test using formation conditions expected for the subterranean formation.

8. The method of claim 1, wherein at least some of the plurality of particulates are coated with a hydrophobic coating material.

9. A method comprising:
   providing particulate pack comprising a plurality of particulates, wherein at least a portion of the particulates of the particulate pack is coated with a ceramic coating ranging between about 100 nm and about 500 nm in thickness;
   allowing an aqueous fluid to flow through the particulate pack; and
   allowing the ceramic coating to impede aqueous fluid interactions between the aqueous fluid and the particulate pack.

10. The method of claim 9, wherein the ceramic coating is present on the particulates in an amount of between about 0.1% to about 10% by weight of the particulates.

11. The method of claim 9, wherein some of the particulates of the particulate pack are coated with a second ceramic coating to form a plurality of ceramic layers.

* * * * *